United States Patent [19]

Jensen

[11] Patent Number: 5,747,257
[45] Date of Patent: May 5, 1998

[54] **GENETIC MARKERS AND METHODS FOR THE DETECTION OF *ESCHERICHIA COLI* SEROTYPE-0157:H7**

[75] Inventor: Mark Anton Jensen, West Chester, Pa.

[73] Assignee: E. I. du Pont de Nemours and Company, Wilmington, Del.

[21] Appl. No.: 608,881

[22] Filed: Feb. 29, 1996

[51] Int. Cl.$^6$ .............. C12Q 1/68; C12P 19/34; C07H 21/04
[52] U.S. Cl. .......... 435/6; 435/91.2; 536/24.3; 536/24.32; 536/24.33
[58] Field of Search ............ 435/6, 91.2; 536/24.3, 536/24.32, 24.33

[56] References Cited

U.S. PATENT DOCUMENTS

| | | | |
|---|---|---|---|
| 4,717,653 | 1/1988 | Webster, Jr. | 435/5 |
| 5,087,558 | 2/1992 | Webster, Jr. | 435/5 |
| 5,126,239 | 6/1992 | Livak et al. | 435/6 |
| 5,340,728 | 8/1994 | Grosz et al. | 435/91.2 |

FOREIGN PATENT DOCUMENTS

| | | | |
|---|---|---|---|
| 2055302 | 5/1992 | Canada | C12Q 1/68 |
| 0 517 154 A1 | 12/1992 | European Pat. Off. | C12Q 1/68 |
| 0 517 361 A1 | 12/1992 | European Pat. Off. | C12Q 1/68 |
| 0 543 484 A2 | 5/1993 | European Pat. Off. | C12Q 1/68 |
| WO 90/11370 | 10/1990 | WIPO | C12Q 1/68 |
| WO 90/15157 | 12/1990 | WIPO | C12Q 1/68 |
| WO 92/03567 | 3/1992 | WIPO | C12P 19/34 |
| WO 92/07095 | 4/1992 | WIPO | C12Q 1/68 |
| WO 92/07948 | 5/1992 | WIPO | C12P 19/34 |
| WO 92/14844 | 9/1992 | WIPO | C12Q 1/68 |
| 94/13832 | 6/1994 | WIPO | |
| WO95/33854 | 12/1995 | WIPO | C12Q 1/68 |

OTHER PUBLICATIONS

Enns, Russel K., *Lab. Med.*, 19(5), 295–300 (1988).
Mordarski, M., *Soc. Appl. Bacteriol. Tech.*, Ser., 20 (Chem. Methods for Bact. Syst.) 41–66 (1985).
Samadpour, M., *J. Clin. Microbiol.*, 33(8), 2150–2154 (1995).
Landry, B.S. et al, *Genome*, 36, 580–587 (1993).
vanBelkum, A. et al, *Mol. Biochem Parasitol* 61, 69–78 (1993).
Ramotar, K. et al, *J. Clin. Microbiol.*, 33(3), 519–524 (1995).
Fratamico, P.M. et al, *J. Clin. Microbiol.*, 33(8), 2188–2191 (1995).
Southern, E.M., *J. Mol. Biol.*, 98, 503–517 (1975).
Botstein, D. et al, *Am. J. Hum. Genet.*, 342, 314–331 (1980).
Williams, J.G.K. et al, *Nucl. Acids. Res.*, 18(22), 6531–6535 (1990).
Madico et al., *J. Clin. Micro.* 33(6), 1534–1536 (1995).
Heuvelink et al., Epidemiol. Infect. 115, 1–14 (1995).

*Primary Examiner*—Kenneth R. Horlick

[57] ABSTRACT

A method, diagnostic sequences and primers are provided that are useful in the identification of the *Escherichia coli* 0157:H7 serotype. The method first involves the identification of a RAPD-amplified DNA fragment common to 0157:H7 *Escherichia coli*, the identification of the most conserved regions of that fragment, and the preparation of specific primers useful for detecting the presence of a marker within the fragment whereby that set of primers is then useful in the identification of all 0157:H7 *Escherichia coli*.

7 Claims, 6 Drawing Sheets

```
     12CN07
     GGCATTAGTCACGCAATGAATGGCACACAGGAGCGTGAATTATCGCTGGCTGAATTATCC
1    ------------+---------+---------+---------+---------+---------+   60
     CCGTAATCAGTGCGTTACTTACCGTGTGTCCTCGCACTTAATAGCGACCGACTTAATAGG 77-23-114
                              ┌─────────────────────┐
                              │     77-26-111       │
                              │┌──────────────┐     │
     TGGTGGGCGGCCTGCAATCAGGTGGTGGATGCACTACCTGAGGCAGTAGCGCGTCGTTCG
61   ------------+---------+---------+---------+---------+---------+   120
     ACCACCCGCCGGACGTTAGTCCACCACCTACGTGATGGACTCCGTCATCGCGCAGCAAGC

CTGGGATTACCAGCGGAAAAAATCCGCTCCGTATACCGTGAGAGTGACATCGCACCGGGA
121  ------------+---------+---------+---------+---------+---------+   180
     GACCCTAATGGTCGCCTTTTTTAGGCGAGGCATATGGCACTCTCACTGTAGCGTGGCCCT

GAACAGACAGCCATCAGCATACTGAAGCAGCGCACAAAAAATATTGCGCTGCCACTTCAC
181  ------------+---------+---------+---------+---------+---------+   240
     CTTGTCTGTCGGTAGTCGTATGACTTCGTCGCGTGTTTTTTATAACGCGACGGTGAAGTG

GTCCACCAGCAACAAAATCCACCACAGAAAAAAACGGTTGTCAGTATCGCCGTTGATCCG
241  ------------+---------+---------+---------+---------+---------+   300
     CAGGTGGTCGTTGTTTTAGGTGGTGTCTTTTTTTGCCAACAGTCATAGCGGCAACTAGGC

GAGTCTCCTGAATCGTTCATGAGGCGGCCTAAACGTTGCCGCTGGGTTAATGAGAAATAC
301  ------------+---------+---------+---------+---------+---------+   360
     CTCAGAGGACTTAGCAAGTACTCCGCCGGATTTGCAACGGCGACCCAATTACTCTTTATG

ACGCGCTGGGTAAAGACACAGCCGTGTGCGTGTTGTGGTAAGCCTGCTGACGATCCGCAT
361  ------------+---------+---------+---------+---------+---------+   420
     TGCGCGACCCATTTCTGTGTCGGCACACGCACAACACCATTCGGACGACTGCTAGGCGTA

CACCTGATTGGTCATGGTCAGGGGGGAATGGGGACAAAGGCCCACGATATTTTCACGCTA
421  ------------+---------+---------+---------+---------+---------+   480
     GTGGACTAACCAGTACCAGTCCCCCCTTACCCCTGTTTCCGGGTGCTATAAAAGTGCGAT 77-26-538
     CCGTTGTGCCGGGAGCACCACAACGAACTTCATGCAGACCCGCTGGAGTTTGAGAAAAAG
481  ------------+---------+---------+---------+---------+---------+   540
     GGCAACACGGCCCTCGTGGTGTTGCTTGAAGTACGTCTGGGCGACCTCAAACTCTTTTTC

TACGGCTCTCAGATTGAGTTAATTTTTCGTTTTCTTGATCACGCCTTTGCGACTGGCGTG
541  ------------+---------+---------+---------+---------+---------+   600
     ATGCCGAGAGTCTAACTCAATTAAAAAGCAAAGAACTAGTGCGGAAACGCTGACCGCAC
                77-23-rc536

CTCGGGTAAAGAGGTGACTGATGCTCATAGATTTGGTTTTACCTTACCCGCCGACGGTG
601  ------------+---------+---------+---------+---------+---------+   660
     GAGCCCATTTTCTCCACTGACTACGAGTATCTAAACCAAAATGGAATGGGCGGCTGCCAC
                    12CN07
```

FIG.2A

```
     AACACCTACTGGCGACGTCGTGGCAGCACATATTTTGTATCAAAAGCCGGTGAGCGTTAT
661  ------------------------------------------------------------  720
     TTGTGGATGACCGCTGCAGCACCGTCGTGTATAAAACATAGTTTTCGGCCACTCGCAATA

CGCCGGGCTGTGGCGCTTATTGTTCGCCAGCAGCGGCTGAAATTAAGCCTGTCCGGAAGG
721  ------------------------------------------------------------  780
     GCGGCCCGACACCGCGAATAACAAGCGGTCGTCGCCGACTTTAATTCGGACAGGCCTTCC

CTGGCGATGAAGATTATTGCCGAGCCACCGGATAAGCGCCGCCGTGACCTGGACAATGTT
781  ------------------------------------------------------------  840
     GACCGCTACTTCTAATAACGGCTCGGTGGCCTATTCGCGGCGGCACTGGACCTGTTACAA

CTGAAAGCGCCGCTGGATGCGCTGACGCATGCGGGGTTGCTAATGGACGATGAGCAGTTT
841  ------------------------------------------------------------  900
     GACTTTCGCGGCGACCTACGCGACTGCGTACGCCCCAACGATTACCTGCTACTCGTCAAA

GATGAAATCAATATTGTGCGCGGTCAGCTCGTTCCTGGTGAGCGGCTGGGGATAAAAATC
901  ------------------------------------------------------------  960
     CTACTTTAGTTATAACACGCGCCAGTCGAGCAAGGACCACTCGCCGACCCCTATTTTTAG

ACAGAACTGGAGTGCGCATGAATAACCACTATTTACAGTTTGTGCGTGAGCTGCTCATTA
961  ------------------------------------------------------------ 1020
     TGTCTTGACCTCACGCGTACTTATTGGTGATAAATGTCAAACACGCACTCGACGAGTAAT
                                                            └──────

TCGCTACTGCCTCAGGTAGTGCATCCA
1021 --------------------------- 1047
     AGCGATGACGGAGTCCATCACGTAGGT
     └────────────────────────┘
            77-26-111
     ├──────────────────────┤
          7111-26-rc1012
```

GENETIC MARKERS AND METHODS FOR THE DETECTION OF *ESCHERICHIA COLI* SEROTYPE-0157:H7

FIELD OF INVENTION

The invention relates to the field of molecular biology and the use of randomly amplified nucleic acid fragments for the selection of genetic markers useful in the identification of bacteria. More specifically, the invention relates to a specific DNA marker sequence useful for the detection of *E. coli* serotype 0157:H7 and use of that diagnostic marker to determine if an unknown bacterium is a member of the 0157:H7 serotype.

BACKGROUND

Central to the field of microbiology is the ability to positively identify microorganisms at the level of genus, species or serotype. Correct identification is not only an essential tool in the laboratory, but it plays a significant role in the control of microbial contamination in the processing of food stuffs, the production of agricultural products, and the monitoring of environmental media such as ground water. Increasing stringency in regulations which apply to microbial contamination have resulted in a corresponding increase in industry resources which must be dedicated to contamination monitoring.

Of greatest concern is the detection and control of pathogenic microorganisms. Although a broad range of microorganisms have been classified as pathogenic, attention has primarily focused on a few bacterial groupings such as Escherichia, Salmonella, Listeria and Clostridia. Typically, pathogen identification has relied on methods for distinguishing phenotypic aspects such as growth or motility characteristics, and for immunological and serological characteristics. Selective growth procedures and immunological methods are the traditional methods of choice for bacterial identification and these can be effective for the presumptive detection of a large number of species within a particular genus. However, these methods are time consuming and are subject to error. Selective growth methods require culturing and subculturing in selective media, followed by subjective analysis by an experienced investigator. Immunological detection (e.g., ELISA) is more rapid and specific, however, it still requires growth of a significant population of organisms and isolation of the relevant antigens. For these reasons interest has turned to detection of bacterial pathogens on the basis of nucleic acid sequence.

It is well known, for example, that nucleic acid sequences associated with the ribosomes of bacteria are often highly conserved across genera and are therefore useful for identification (Webster, U.S. Pat. No. 4,717,653 and U.S. Pat. No. 5,087,558; Enns, *Lab. Med.*, 19, 295, (1988); Mordarski, *Soc. Appl. Bacteriol. Tech.* Ser., 20 (Chem. Methods Bact. Syst.), 41, (1985)). Weisburg et al. (EP 51736) disclose a method for the detection and identification of pathogenic microorganisms involving the PCR amplification and labeling of a target nucleotide for hybridization to 16S rDNA of *E. coli*. Lane et al. (WO 9015157) teach universal nucleic acid probes that hybridize to conserved regions of 23S or 16S rRNA of eubacteria.

Although bacterial ribosomal nucleic acids contain highly conserved sequences, they are not the only sources of base sequence conservation that is useful for microorganism identification. Wheatcroft et al. (CA 2055302) describe the selection of transposable elements, flanked by unique DNA sequences, for the detection of various Rhizobium strains. Similarly, Tommassen et al. (WO 9011370) disclose polynucleotide probes and methods for the identification and detection of gram-positive bacteria. The method of Tommassen et al. relies on probes corresponding to relatively short fragments of the outer membrane protein OmpA, known to be highly conserved throughout gram-positive genera. Atlas et al. (EP 517154) teach a nucleic acid hybridization method for the detection of Giardia sp. based on designing probes with sequences complementary to regions of the gene encoding the giardin protein. Webster et al. (U.S. Pat. No. 4,717,653) has expanded upon the use of rRNA in disclosing a method for the characterization of bacteria based on the comparison of the chromatographic pattern of restriction endonuclease-digested DNA from the unknown organism with equivalent chromatographic patterns of at least 2 known different organism species. The digested DNA has been hybridized or reassociated with ribosomal RNA information-containing nucleic acid from, or derived from a known probe organism. The method of Webster et al. effectively establishes a unique bacterial nucleic acid "fingerprint" corresponding to a particular bacterial genus against which unknown "fingerprints" are compared.

Similar methods have been use for the detection of *E. coli* 0157:H7. For example, Samadour (*J. Clin. Microbiol.* (1995), 33(8), 2150–4) teaches the detection of *E. coli* 0157:H7 by restriction fragment length polymorphism using Shiga-like toxin genes which are conserved between the 0157:H7 serotype and *shigella*. Similarly, Ramotar et al. (*J. Clin. Microbiol.* (1995), 33(3), 519–24) and Fratamico et al. (*J. Clin. Microbiol.* (1995), 33(8), 2188–91) teach PCR based methods for the detection of conserved 0157:H7 genes encoding either shiga-like toxins or verotoxins.

The methods described above are useful for the detection of bacteria, but each relies upon knowledge of a gene, protein, or other specific sequence known a priori to be highly conserved throughout a specific bacterial group. An alternative method would involve a nontargeted analysis of bacterial genomic DNA for specific non-phenotypic genetic markers common to all species of that bacteria. For example, genetic markers based on single point mutations may be detected by differentiating DNA banding patterns from restriction enzyme analysis. As restriction enzymes cut DNA at specific sequences, a point mutation within this site results in the loss or gain of a recognition site, giving rise in that region to restriction fragments of different length. Mutations caused by the insertion, deletion or inversion of DNA stretches will also lead to a length variation of DNA restriction fragments. Genomic restriction fragments of different lengths between genotypes can be detected on Southern blots (Southern, *J. Mol. Biol.* 98, 503, (1975)). The genomic DNA is typically digested with any restriction enzyme of choice, the fragments are electrophoretically separated, and then hybridized against a suitably labelled probe for detection. The sequence variation detected by this method is known as restriction length polymorphism or RFLP (Botstein et al., *Am. J. Hum. Genet.* 342, 314, (1980)). RFLP genetic markers are particularly useful in detecting genetic variation in phenotypically silent mutations and serve as highly accurate diagnostic tools.

Another method of identifying genetic polymorphic markers employs DNA amplification using short primers of arbitrary sequence. These primers have been termed "random amplified polymorphic DNA" or "RAPD" primers (see Williams et al., *Nucl. Acids. Res.*, 18, 6531 (1990) and U.S. Pat. No. 5,126,239; also EP 0 543 484 A2, WO 92/07095, WO 92/07948, WO 92/14844, and WO 92/03567). The RAPD method amplifies either double or single stranded nontargeted, arbitrary DNA sequences using standard amplification buffers, DATP, dCTP, dGTP and TTP and a thermostable DNA polymerase such as Taq. The nucleotide sequence of the primers is typically about 9 to 13 bases in length, between 50 and 80% G+C in composition and contains no palindromic sequences. RAPD detection of genetic polymorphisms represents an advance over RFLP in that it is less time consuming, more informative, and readily susceptible to automation. Because of its sensitivity for the detection of polymorphisms, RAPD analysis and variations based on RAPD/PCR methods have become the methods of choice for analyzing genetic variation within species or closely related genera, both in the animal and plant kingdoms. For example, Landry et al. (*Genome*, 36, 580, (1993)) discuss the use of RAPD analysis to distinguish various species of minute parasitic wasps which are not morphologically distinct. Van Belkum et al. (*Mol. Biochem Parasitol* 61, 69, (1993)) teach the use of PCR-RAPD for the distinction of various species of Giardi.

In commonly assigned application U.S. Ser. No. 07/990, 297, U.S. Pat. No. 5,340,728, Applicants disclose a method of double-nested PCR which is used to detect the presence of a specific microbe. This disclosure first describes identifying a random, unique segment of DNA for each individual microorganism which will be diagnostic for that microorganism. To identify and obtain this diagnostic nucleic acid segment a series of polymorphic markers is generated from each organism of interest using single primer RAPD analysis. The RAPD series from each organism is compared to similarly generated RAPD series for other organisms, and a RAPD marker unique to all members of the group is then selected. The unique marker is then isolated, amplified and sequenced. Outer primers and inner primers suitable for double-nested PCR of each marker may then be developed. These primers comprise sequence segments within the RAPD markers, wherein the inner set of primers will be complementary to the 3' ends of the target piece of nucleic acid. These nested primers may then be used for nested PCR amplification to definitely detect the presence of a specific microorganism.

In commonly owned PCT U.S. 95/06704, Applicants have more particularly adapted and described this RAPD methodology to identify a sequence, or marker. The presence of the marker is diagnostic for all individuals of the genus Salmonella. U.S. Ser. No. 08/254,355 teaches a method involving a RAPD amplification of genomic DNA of a representative number of Salmonella individuals to produce a RAPD amplification product, termed the diagnostic fragment. This diagnostic fragment must be present in the RAPD profiles in over 90% of the individuals tested. Sequence information from the diagnostic fragment enables identification of the most suitable PCR primer binding sites within the diagnostic fragment to define a unique diagnostic marker. Primers flanking this marker are useful for the generation of amplification products from Salmonella genomic DNA, but will not produce any amplification products in non-Salmonella genera.

A detection methodology using PCR/RAPD specific to *Escherichia coli* 0157:H7 serotypes would be of high utility in the food industry. Detection methods not dependent on sequences derived from a known gene or associated with a known phenotypic characteristic of *E. coli* 0157:H7 serotype have not previously been disclosed.

SUMMARY OF THE INVENTION

The present invention provides a method for the determination of diagnostic genetic markers for the specific identification of *E. coli* 0157:H7 serotype. The method comprises the following steps:

(i) performing a RAPD amplification on the genomic DNA of a representative number of individual *E. coli* 0157:H7 strains. These strains comprise the positive test panel. RAPD amplification performed on individuals of the positive test panel will generate a RAPD marker profile from each individual. The same RAPD amplification is performed on the genomic DNA of a significant number of individuals genetically unrelated to the positive test panel. In the present application non-0157:H7 *E. coli* made up the negative test panel. RAPD amplifcation of the members of the negative test panel generated individual RAPD marker profiles as with the postive test panel;

(ii) comparing the RAPD marker profiles from individuals of the positive test panel with the RAPD marker profiles from individuals of the negative test panel and selecting a diagnostic nucleic acid fragment where the fragment is present in all of the RAPD marker profiles from the positive test panel and absent in the RAPD marker profiles from the negative test panel;

(iii) determining the nucleotide sequence of the diagnostic fragment to identify available primer binding sites;

(iv) preparing one or more pairs of primers corresponding to the available primer binding sites of step (iii);

(v) performing primer-directed amplification on the genomic DNA from members of the positive test panel using the primer pairs of step (iv). The amplification products of this step are compared against similar products generated by amplifications with the same primers against the negative test panel. Primers producing amplification products only in 0157:H7 serotypes and not in any other *E. coli* strains are then selected for their ability to amplify a specific 0157:H7 diagnostic marker.

(vi) Finally, the specificity of the primers selected in (v) are confirmed in a PCR assay against a large panel of 0157:H7 and non-0157:H7 strains.

In a preferred embodiment, the invention identifies the presence of 0157:H7 *E. coli* serotype by means of a PCR amplification assay using a first primer derived from a nucleic acid sequence (SEQ ID NO.: 1) and identified as SEQ ID NOS.: 3, 5, 7, and 9 and a second primer derived from a nucleic acid sequence (SEQ ID NO.: 2) and identified as SEQ ID NOS.: 4, 6, 8, and 10.

A further embodiment of the method uses a nucleic acid probe of a sequence complementary to that of a nucleic acid sequence (SEQ ID NOS.: 1 or 2 or a diagnostic marker fragment thereof). The nucleic acid probe hybridizes to the nucleic acid sequence acid and is detected. The presence of the hybridzed probe indicates the presence of the target nucleic acid sequence which in turn indicates the presence of a member of the *E. coli* 0157:H7 serotype.

This invention further provides isolated nucleic acid fragments having SEQ ID NOS.: 1–14.

BRIEF DESCRIPTION OF THE FIGURES

FIG. 2 is the complete marker sequence illustrating the primer binding sites for the diagnostic primers 12CN07 (SEQ ID NO: 3and its reverse complement, SEQ ID NO: 4), 77-23-114, 77-26-111 (SEQ ID NO: 5 and its reverse complement, SEQ ID NO: 6), 77-26-538, 77-23-rc536, and 7111-26-rc1012.

DETAILED DESCRIPTION OF THE INVENTION

Figure 1:
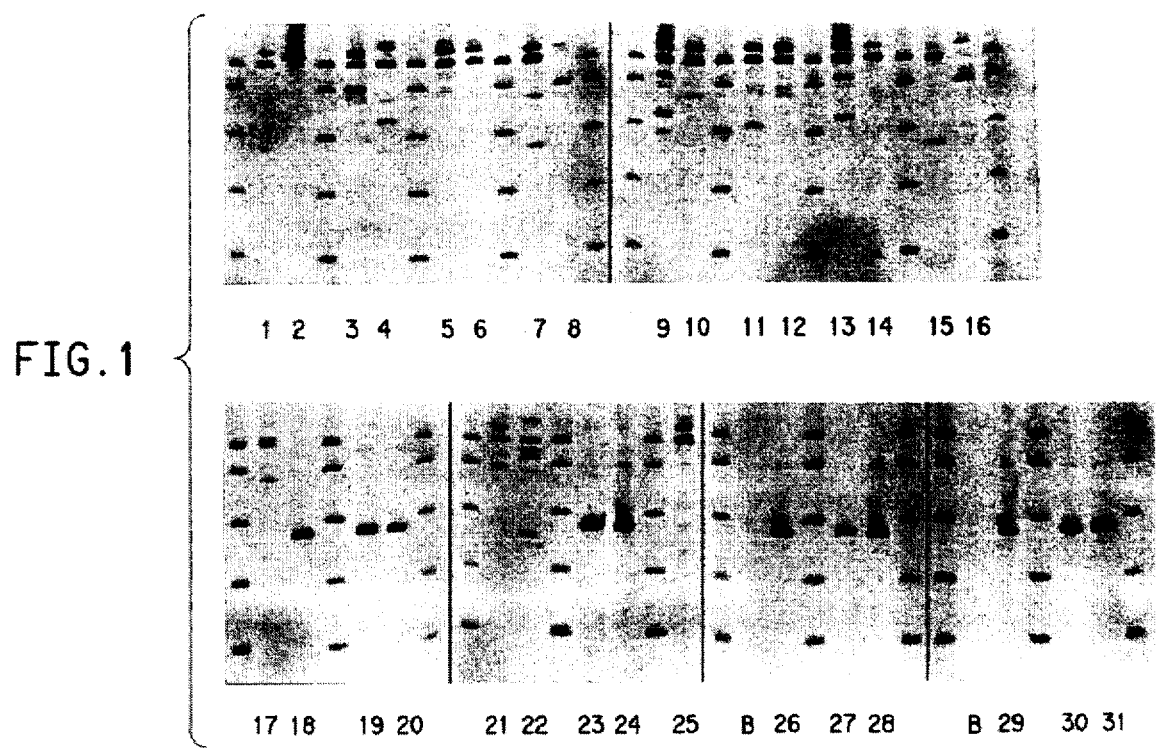
FIG. 1 is a gel showing RAPD patterns for *E. coli* strains comprising both the negative and positive test panels, amplified with the 12-mer primer 12CN07 (Table I).

In the present method, Applicant has used RAPD amplification of 0157:H7 genomic DNA to discover diagnostic fragments and primers useful for the specific detection of E. coli 0157:H7 serotypes. The fragment is used to generate specific primers from the most conserved regions of the fragment for use in a PCR assay that will only produce an amplification product from a 0157:H7 genome. No amplification products are seen with non-0157:H7 E. coli.

Applicant's method is distinctive in the following regard. To selectively detect only the 0157:H7 serotype from all other E. coli strains the method must be sucessful in determining the most conserved regions of the diagnostic fragment from a phenotypically uncharacterized segment of DNA common to all members of the Escherichia genus. One of skill in the art will recognize that conservation of sequence may be both an ally and an enemy in identifying the members of a particular genus. For example, many bacterial sequences are conserved across genera and hence these would not be useful in the determination of species within a particular genus. It is precisely for that reason that methods heretofore elucidated in that art rely primarily on the analysis of sequences derived from proteins or genes known to be specific to a particular genus, i.e., ribosomal RNA or toxin encoding genes. Applicant's method departs from the art in that the conserved sequences of the instant method are not derived from a known gene, nor is the sequence associated with any known phenotypic characteristic.

As used herein the following terms may be used for interpretation of the claims and specification.

"Nucleic acid" refers to a molecule which can be single stranded or double stranded, comprising monomers (nucleotides) containing a sugar, phosphate and either a purine or pyrimidine. In bacteria, lower eukaryotes, and in higher animals and plants, "deoxyribonucleic acid" (DNA) refers to the genetic material while "ribonucleic acid" (RNA) is involved in the translation of the information from DNA into proteins.

The term "primer-directed amplification" refers to any of a number of methods known in the art that result in logarithmic amplification of nucleic acid molecules using the recognition of a specific nucleic acid sequence or sequences to initiate an amplification process. Applicants contemplate that amplification may be accomplished by any of several schemes known in this art, including but not limited to the polymerase chain reaction (PCR) or ligase chain reaction (LCR). If PCR methodology is selected, the amplification method would include a replication composition consisting of, for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis et al.) and U.S. Pat. No. 4,683,195 (1986, Mullis et al.).

A "diagnostic fragment" refers to a particular DNA sequence which is highly conserved amongst the individuals of a particular genetically related population, for example, a genus, species, or serotype of bacteria. In the instant invention, the term "diagnostic fragment" is used to refer to that fragment generated during RAPD amplification which is present in the RAPD profiles from all E. coli 0157:H7 serotypes, but absent in profiles from non-0157:H7 serotypes. The term "diagnostic marker" is used herein to refer to that portion of the diagnostic fragment which can be targeted to produce an amplification product only in E. coli 0157:H7. The diagnostic marker is not present in non-0157:H7 E. coli and attempts to amplify the diagnostic markers in non-0157:H7 individuals will give no amplification product. Diagnostic fragments which are markers for E. coli 0157:H7 and useful in Applicant's invention include nucleic acid sequences SEQ ID NOS.: 1–14 and fragments thereof.

The term "primer" refers to a nucleic acid fragment or sequence that is complementary to at least one section along a strand of the sample nucleic acid, wherein the purpose of the primer is to sponsor and direct nucleic acid replication of a portion of the sample nucleic acid along that string. Primers can be designed to be complementary to specific segments of a targeted sequence. In PCR, for example, each primer is used in combination with another primer forming a "primer set" or "primer pair"; this pair flanks the targeted sequence to be amplified. In RAPD amplification, single arbitrary primers are used to amplify nontargeted segments of nucleic acid which are located between the primer sequence sites in opposing DNA strands. The term "primer", as such, is used generally herein by Applicants to encompass any sequence-binding oligonucleotide which functions to initiate the nucleic acid replication process. "Diagnostic primers" will refer to primers designed with sequences complementary to primer binding sites on the diagnostic marker. Diagnostic primers are useful in the convenient detection and identification of diagnostic markers specific to E. coli 0157:H7.

A genetically related population refers to any grouping of microorganisms possessing multiple or single phenotypic characteristics of sufficient similarity to allow said organisms to be classified as a single genus, species, or subspecies of bacteria. For purposes of the present disclosure, examples of genetically related populations include, for example, the E. coli serotype0157:H7.

A "test panel" refers to a particular group of organisms or individuals selected on the basis of their genetic similarity to each other or on the basis of their genetic dissimilarity to another group (i.e., another genus, species, subspecies or serotype). A "positive test panel" will refer to a number of individuals selected for the desired genetic similarity between those individuals and, in the instant case, will be comprised of individuals of the 0157:H7 E. coli serotype.

The term "unknown microorganism" or "unknown bacterium" is a microorganism or bacterium whose identity is undetermined.

Similarly, a "negative test panel" will refer to a test panel selected on the basis of genetic diversity between its members and the members of the positive test panel. A suitable negative test panel in the present invention would be comprised of non-0157:H7 *E. coli* bacterial strains.

The term "amplification product" refers to specific DNA fragments generated from any primer-directed nucleic acid amplification reaction. The diagnostic markers of the present invention are amplification products generated in PCR reaction using diagnostic primers and are useful for the detection of *E. coli* 0157:H7 serotype bacteria.

The term "derived from", with reference to an amplification primer, refers to the fact that the sequence of the primer is a fragment of the sequence from which it has been "derived". The fragment is always denoted in a 5' to 3' orientation. The useful primer sequence size range for PCR amplification is about 15 base pairs to about 30 base pairs in length.

The term "RAPD" refers to 'random amplified polymorphic DNA'. "RAPD amplification" refers to a method of single primer-directed amplification of nucleic acids using short primers of arbitrary sequence to amplify nontargeted, random segments of nucleic acid. The method is disclosed and claimed in U.S. Pat. No. 5,126,239. "RAPD method" or "RAPD analysis" refers to a method for the detection of genetic polymorphisms involving the nontargeted amplification of nucleic acids using short primers of arbitrary sequence, whereby the profile or pattern of 'RAPD' amplification products is compared between samples to detect polymorphisms. "RAPD primers" refers to primers of about 8 to 13 bp, of arbitrary sequence, useful in the RAPD amplification or RAPD analysis according to the instant method. The "RAPD marker profile" refers to the pattern, or fingerprint, of amplified DNA fragments which are amplified during the RAPD method and separated and visualized by gel electrophoresis.

The diagnostic marker of the invention can be used to identify any member of the *E. coli* 0157:H7 serotype to the exclusion of all other bacterial genera and all other *E. coli* species and strains. In the present invention, diagnostic primers flanking the marker are useful to amplify the marker using PCR. Alternatively, nucleic acid probes could be developed based upon some or all of the diagnostic marker sequences and thus used to detect the presence of the marker sequence using standard solid phase or solution nucleic acid hybridization and reporter methods. It is contemplated that regions of about 30 base pairs or more of the diagnostic marker, especially encompassing the primer regions could be used as sites for hybridization of diagnostic probes. These methods might be employed specifically for the detection of 0157:H7 serotype in food, human or animal body fluids or tissues, environmental media or medical products and apparatti.

To practice the instant method, a RAPD amplification, using a short arbitrary primer, is performed on the genomic DNA of a positive and negative test panel of bacteria. The positive test panel consisted of members of *E. coli* 0157:H7 serotype. The negative test panel consisted principally of non-0157:H7 *E. coli* strains. The electrophoreticaUy resolved patterns of amplification products produced by the RAPD amplifications were then compared. A distinctive RAPD amplification product, present in all of the individuals tested in the positive test panel and absent in the members of the negative test panel was identified and sequenced. Sequencing revealed suitable primer sites which were used to determine suitable primer binding sites for further analysis and primer generation.

The method is more particularly described below with reference to the specific method steps as provided in the Summary of the Invention.

Selection of RAPD Primers and Detection of Diagnostic Fragment in Members of the Positive and Negative Test Panels, Steps (i) and (ii)

Genomic DNA isolated from positive and negative test panels of microorganisms was subjected to RAPD amplification using eight 12-base primers of arbitrary sequence. The positive test panel consisted of 12 strains of *E. coli* 0157:H7 and is described in detail in the GENERAL METHODS section below. The negative test panel consisted of a variety of 88 non-0157:H7 *E. coli* serotypes and is also described in the GENERAL METHODS section below. Techniques for the isolation of genomic DNA are common and well known in the art and examples may be found in Sambrook et al., Molecular Cloning: A Laboratory Manual—volumes 1,2,3 (Cold Spring Harbor Laboratory: Cold Spring Harbor, New York).

RAPD primers of 12 bases in length were used because at this primer length the RAPD patterns generally contained one to five amplified DNA fragments. Use of shorter primers frequently resulted in a large number of amplification products, which made the extraction of a single homogeneous fragment for sequencing much more difficult. When primers of greater than 12 bases were used a significant fraction of the bacterial strains produced no RAPD products which would have necessitated the screening of a much larger number of arbitrary primers. One of the primers, designated 12CN07 (Table I, GENERAL METHODS), was found to produce a 626 bp amplification product in all of the positive test panel. 12CN07 had the sequence of GGC ATT AGT CAC (SEQ ID NO.: 3). The 626 bp fragment was not seen in the amplification products of the negative test panel with primer 12CN07. (FIG. 1)

Sequencing of Diagnostic Fragment, Step (iii)

The 626 bp product was selected for extraction and sequencing from 0157:H7 genomic DNA. Since the 12CN07 primer generated a single product in the amplification of 0157:H7 genomic DNA, isolation of the product by gel electrophoresis was not required.

Sequencing began by using the 12CN07 primer sequence, since this was the only component of the RAPD product that was known. One of the 12CN07 sequences was removed from the RAPD product by digestion with a select group of 4, 5 and 6 base cutting restriction enzymes. Restriction enzymes that cut the RAPD product near one of the 12CN07 sequences produced digest products that could be directly sequenced without further purification. Although overlapping sequence data occurred up to the digest site, only sequence from the undigested end was observed after that point.

The complete sequence of the 626 bp 0157:H7 product is shown in FIG. 2 representing SEQ ID NO.: 11. Primers generated from the sequence of the 626 bp fragment are fully described in the EXAMPLES and GENERAL METHODS section and in Table II, Example 3.

Identification of Regions of the Diagnostic Fragment Suitable as Primer Binding Sites, Steps (iv) and (v)

Primers were first evaluated for their ability to specifically amplify from 0157:H7 genomic DNA. Initial primer sets were selected to achieve a GC composition of 50±5% within in a distance of 200 bases from each 12CN07 priming site. These primer sequences were also examined to insure that inter- and intra-primer interactions, which might produce nonspecific PCR artifacts, were minimized. In spite of these precautions, many of the primer sets produced multiple amplification products from genomic *E. coli* DNAs. Although the presence of multiple products made the analysis more difficult, it was possible to identify general locations in the 12CN07 fragment where 0157:H7 selectivity was high.

The second stage of analysis required a finely resolved base-by-base primer screening. The initial criteria for primer selection was that the GC content of the two primers should match and that the overall GC content fell in the range of 50±5%. The second criteria was that the pairs of primers were all located within 200 bases of the 12CN07 priming sites. To find primers that most reliably gave amplification products against 0157:H7 genomic DNA, one of the primer sites identified after sequencing was "locked" while the second priming site was moved upstream or downstream one base at a time. In this way the priming site that most consistently gave amplification products against 0157:H7 DNA was identified and fixed. The second priming site was then "locked" and additional primers were prepared, which moved the first priming site at the other end of the target sequence upstream or downstream one base at a time. In this manner a number of priming sites were identified as likely candidates for a PCR assay for the specific amplification of 0157:H7 genomic DNA. Primers derived from these primer binding sites are listed in Table II, Example 3.

Development of Single and Double Primer Assays

Multiple-product amplifications made identification of true amplification products difficult due to competing products generated by the second primer. One explanation for the presence of multiple PCR products was that sequences within the 12CN07 product occurred as inverted repeats within the genomes of *E. coli* strains comprising the initial positive test panel. To determine which products were the result of inverted repeats of a single primer sequence (i.e., AA or BB priming), amplification reactions were run using single 26-base primers.

It was observed that a significant number of single primers were capable of producing PCR products. It was particularly surprising that one primer, 77-26-111 (SEQ ID NO.: 5), produced a product that was highly 0157:H7 specific. This product contained 535 bp of the original RAPD sequence plus an additional 425 bases. This product was sequenced and is shown in FIG. 2 and as SEQ ID NO.: 1.

Single-Primer PCR Detection

An assay for 0157:H7 using amplification 77-26-111 (Table II, Example 3) as a single primer was evaluated for 305 strains of *E. coli* representing a cross-section of O and H-types. Amplification products were seen in 99% of the 0157:H7 strains tested, 1.5% of the non-0157:H7 enterohemorrhagic *E. coli* tested, and only 0.4% for the non-EHEC *E. coli* tested.

Two-Primer PCR Detection

In the development of the two-primer assay, areas of the 962 bp 0157:H7 product generated from the 77-26-111 were rigorously screened for 0157:H7 specificity. Preliminary analysis of the two 77-26-111 priming sites indicated that the 0157:H7 product selectivity arose primarily from the 77-26-111 priming site on the (−) strand (i.e., the second priming site). Since this site was suspected of having less than perfect homology with the 77-26-111 sequence, priming sites in the region 3–10 bases downstream from this site were rigorously evaluated. A highly selective priming site, 7111-26-rc1012, was identified 9 bases downstream from the second 77-26-111 site.

The use of the 7111-26-rc1012 primer in conjunction with a second primer, 7111-26-538, made to another location known to show a significant level of 0157:H7 selectivity, resulted in a highly selective primer pair. In a 0157:H7 assay using these primers, amplification products were generated in 99.5% of the 0157:H7 tested; 0% in non-0157:H7 EHEC and 2.9% in non-EHEC tested.

EXAMPLES

GENERAL METHODS

Suitable methods of genetic engineering employed herein are described in Sambrook et al., Molecular Cloning: A Laboratory Manual—volumes 1,2,3 (Cold Spring Harbor Laboratory: Cold Spring Harbor, New York, 1989), and in the instructions accompanying commercially available kits for genetic engineering. GeneClean (Bio101 LaJolla, Calif.) was used to isolate nucleic acid fragments from agarose gels and to remove enzymes from restriction digests and was performed as specified by the manufacturer. Unless otherwise specified, all other standard reagents and solutions used in the following examples were supplied by J. T. Baker Co. (Phillipsburg, N.J.).

Construction of Positive and Negative Test Panels

A positive test panel consisting of 12 genotypically different 0157:H7 *E. coli* strains was constructed for the identification of a serotype level 0157:H7 RAPD marker.

The negative test panel in the screening for a RAPD marker specific to *E. coli* 0157:H7 consisted of 88 different non-0157:H7 strains of *E. coli* of differing serotypes.

RAPD Primers

RAPD primers used for amplification of genomic DNA from the positive and negative test panels are given below in Table I.

TABLE I

Twelve-Base Arbitrary Primers Used in the Generation of RAPD Patterns for the Purpose of Identifying a Specific Genus Level Salmonella Marker

| | | |
|---|---|---|
| 12CN01 | AGC TGA TGC TAC | (SEQ. ID NO.: 15) |
| 12CN02 | AGT CGA ACT GTC | (SEQ. ID NO.: 16) |
| 12CN03 | TTA GTC ACG GCA | (SEQ. ID NO.: 17) |
| 12CN04 | TGC GAT ACC GTA | (SEQ. ID NO.: 18) |
| 12CN05 | CTA CAG CTG ATG | (SEQ. ID NO.: 19) |
| 12CN06 | GTC AGT CGA ACT | (SEQ. ID NO.: 20) |
| 12CN07 | GGC ATT AGT CAC | (SEQ. ID NO.: 3) |
| 12CN08 | CGT ATG CGA TAC | (SEQ. ID NO.: 21) |

Example 1

ISOLATION OF DIAGNOSTIC FRAGMENT FROM *E. coli* 0157:H7

RAPD Screen Test Results

A set of eight 12-base primers (Table I) was used in a Random Amplified Polymorphic DNA (RAPD) analysis of 48 strains of *Escherichia coli*, including 7 strains representing serotype 0157:H7. The results of these amplifications were examined for a 0157:H7 specific amplification product that could be easily separated from other RAPD products. Five RAPD primers that showed the promising results were subsequently used in the analysis of 64 additional strains of *E. coli*, including 5 strains of O157:H7.

The primers were used individually and as mixed pairs in the following amplification protocol:

For each 50 µL reaction, 1.5 µL-dNTP mix (5 mM dNTP each), 36.3 µL deionized water, 5 µL—10X reaction buffer (500 mM KCl, 100 mM tris @ pH 8.3, 15 mM MgCl$_2$, 0.003% gelatin), 5 µL —of a single primer (10 mM), 0.4 µL Taq polymerase (5 U/µL), and 1.2 µL Taq dilution buffer (10 mM tris @ pH 8.0 and 1.0% Tween 20) were combined. 1.0 µL - genomic bacterial DNA @ 50 ng/µL was added. The reaction was heated to 94° C. for 2 minutes. Twentyeight cycles of the following temperature cycle were run: 15" @ 94° C., 5' @ 46° C., 2' ramp to 72° C., and 1' @ 72° C. At the conclusion of the cycling the reaction was incubated at 72° C. for 7 minutes. A 5 µL aliquot of the reaction was combined with 2 µL of Ficol-loading buffer and run on a 4% acrylamide gel (29:1)/1.0x TBE.

In this study it was found that amplification with primer 12CN07 generated a RAPD pattern that consisted of only a single 626 bp product (SEQ ID NO: 11) for all 12 strains of O157:H7 *E. coli*. An example of these RAPD gel patterns is shown in FIG. 1. The lanes are correlated with the *E. coli* as follows:

| Lane | Stain No. | Serotype | Lane | Stain No. | Serotype |
|---|---|---|---|---|---|
| 1 | 1802 | 06:HNM | 17 | 1448 | NOT TYPED |
| 2 | 1803 | 025:H- | 18 | 1449 | O157:H7 |
| 3 | 1805 | 0143:HNM | 19 | 1455 | O157:H7 |
| 4 | 1807 | 026:H- | 20 | 1459 | O157:H7 |
| 5 | 1821 | 055:H- | 21 | 1919 | 08:HNM |
| 6 | 1822 | 028:H8 | 22 | 1922 | 063:H6 |
| 7 | 1827 | 020:HNM | 23 | 1977 | O157:H7 |
| 8 | 1828 | 0143:HNM | 24 | 1979 | O157:H7 |
| 9 | 1857 | 0144:H42 | 25 | 2019 | 148:H- |
| 10 | 1860 | 0126:H27 | 26 | 914 | O157:H7 |
| 11 | 1862 | 027:HNM | 27 | 915 | O157:H7 |
| 12 | 1872 | 0126:H10 | 28 | 916 | O157:H7 |
| 13 | 1883 | 0125:HNM | 29 | 640 | O157:H7 |
| 14 | 1886 | 0164:HNM | 30 | 641 | O157:117 |
| 15 | 1889 | 0152:H10 | 31 | 642 | O157:H7 |
| 16 | 1908 | 025:H7 | | | |

Blank lanes are designated with the letter "B". Unlabeled lanes contain molecular weight markers of the following sizes: 228, 412, 693, 1331, and 2306 bps. Of the remaining 100 strains of non-O157:H7 only 2 strains produced this product. This 626 bp product was isolated for further characterization.

As is evident from FIG. 1, the positive test panel produced a characteristic amplification product of 626 bp which appeared in all of the 12 *E. coli* O157:H7 strains tested.

As is evident from the data in FIG. 1, none of the negative test panel group showed the 626 bp amplification product seen in the positive test panel.

Example 2

Extraction and Sequencing of the *E. coli* O157:H7 Diagnostic Fragment

The 626 bp product for DuPont No.641 *E. coli* (ATCC 43890, American Type Culture Collection, Rockville, Md.) a well-characterized ATCC strain of O157:H7, was selected for sequencing. Since 12CN07 generated single product in the amplification of O157:H7 genomic DNA, isolation of the product by gel electrophoresis was not required.

Sequencing the 12CN07 RAPD product was accomplished using the chain-termination method of Sanger et al. (*Proc. Natl. Acad. Sci., USA* 74, 5463, (1977)) using fluorescence-labeled dideoxynucleotides and the Genesis™ DNA Analysis System (E. I. du Pont de Nemours and Company, Wilmington, Del.).

The first step in the sequencing process requires use of the 12CN07 primer sequence, since this is the only component of the RAPD product that is known. To use 12CN07 as a primer sequence, it was necessary to remove one of the 12CN07 sequences from the RAPD product. When this is not done, reactions using a 12CN07 primer generate sequencing products from both ends of the RAPD product. Such a mixture of overlapping sequencing products can not be used to reliably determine nucleotide composition.

To remove one of the 12CN07 ends, the RAPD product was digested with a select group of 4, 5 and 6 base restriction enzymes. If the restriction enzymes cut the RAPD product near one of the 12CN07 sequences, then the digest product could be directly sequenced without further purification. Although overlapping sequence data occurs up to the digest site, past that point only sequence from the undigested end is observed. The following restriction enzymes cut the RAPD product near the 12CN07 sequence of the −strand: Bcl 1, Bsp 1286 I, Bsr I, and Sau3A I. Products from these digests were used to sequence the +strand. BstN I, BstU I, Fnu4H I, and Hae III cut the RAPD product near the 12CN07 sequence of the +strand. Products from these digests were used to generated sequence of the −strand. Once dissimilar sequences had been identified for both ends of the RAPD product, these sequences could serve as PCR primers and conventional PCR-based sequencing techniques could be used. The complete sequence of the 626 bp O157:H7 product including the flanking 12CN07 sequences is shown in SEQ ID NO.: 3.

Sequencing

Sequencing of the RAPD amplification products was done according to the following protocol:

Combine 1.5 µL - purified digest product (est. 100 ng), 3.5 µL - 12CN07 @ 10.0 ng/µL and 28.5 µL - H$_2$O and heat to 95° C. for 2 minutes. Immediately place the mixture on wet ice. Add the following mixture: 10 µL - 5X reverse tranbscriptase reaction buffer (300 mM tris @ pH 8.3, 375 mM NaCl, 37.5 mM MgCl$_2$), 6.5 µL - dNTP stock (180 uM ea.), 0.65 µL - ddNTP stock (250 µM 505nm-ddGTP, 800 µM 512nm-ddATP, 210 µM 519nm-ddCTP and 700 µM 526 nm-ddTTP) and 1 µL - reverse transcriptase. Vortex, centrifuge and then incubate at 46° C. for 15 minutes. Separate the sequencing products on a spin column and vacumn dry. Wash with 150 µL of cold 70% ethanol and centrifuge 5 minutes. Vacuum dry and reconstitute in 3 µL formamide.

The labeled sequencing products were then analyzed by the Genesis 2000™ DNA Analysis System. Once differential sequence had been determined at both ends of the *E. coli* target fragment the remaining sequence information was obtained through the use of either asymmetric PCR to generate single-stranded DNA or a modified double-stranded DNA sequencing protocol using double-stranded PCR product. The modification in the double-stranded protocol consisted of using a 46° C. annealing temperature and a primer:template ratio of 25:1. This ratio is significantly higher than is generally practiced in sequencing reactions. At such a large primer:template ratio, priming at multiple sites is generally observed with single-stranded templates. However, when the template consists of short linear double-stranded DNA, successful priming can only occur at 5' blunt ends of the template and only with a primer whose sequence matches that end. The net result is that only a single discrete sequencing product is observed under these conditions. The sequence of the complete E. coli fragment is shown in FIG. 2 and in SEQ ID NOS.: 1 and 2.

Example 3

PCR Detction Using An O157:H7 - Specific Rapd Sequence

The following procedure was used to identify the primers most specific for O157:H7 identification, based on the sequence of the diagnostic fragment:

Primers were prepared for a large number sites at both ends of the E. coli O157:H7 target sequence. Amplifications were carried out on genomic DNA from the positive test panel for a variety of these primer combinations according to the protocols listed below. In cases where a given primer combination produced an amplification product in over 95% of the positive test panel, additional primers were then prepared which moved one of the priming sites upstream or downstream one base at a time. Once the priming site that found the highest portion of O157:H7 was identified, that site was fixed and then additional primers were prepared which moved the priming site at the other end of the target sequence upstream or downstream one base at a time. The combination of priming sites which produced an amplification product for the highest percentage O157:H7 in the positive test panel were then evaluated at the next stage of the screening procedure.

The sets of amplification primer pairs selected by this process are listed in Table II.

TABLE II

Primers used in the determination of E. coli O157:H7

| #77-26-111 | TGGATGCACTACCTGAGGCAGTAGCG | (SEQ. ID NO.: 5) |
| #7111-26-rc1012 | TACCTGAGGC AGTAGCGATA ATGAGC | (SEQ. ID NO.: 10) |
| #7111-26-538 | ATGCAGACCCGCTGGAGTTTGAGAAA | (SEQ. ID NO.: 9) |
| #77-23-rc536 | CTCAATCTGA GAGCCGTACT TTT | (SEQ. ID NO.: 8) |
| #77-23-114 | CACTACCTGA GGCAGTAGCG CGT | (SEQ ID NO.: 7) |

Figure 3A:
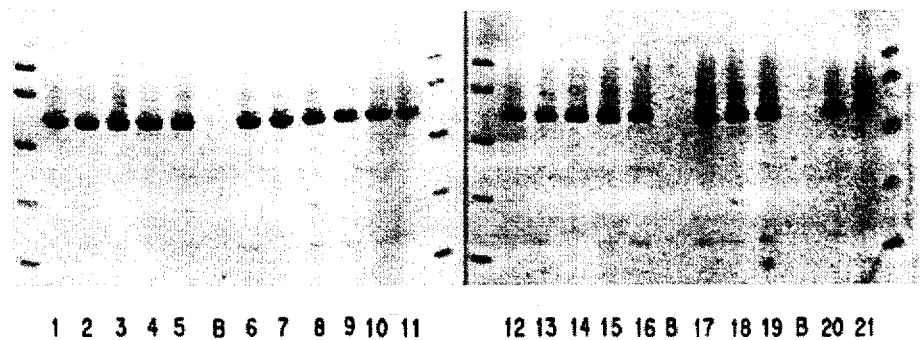
FIG. 3a displays the PCR product patterns of E. coli strains from the positive test panel amplified with the single primer 77-26-111.
Figure 3B:
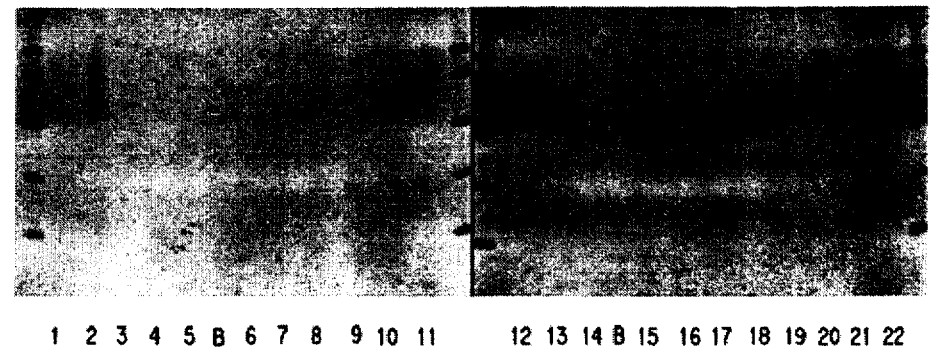
FIG. 3b displays the PCR product patterns of E. coli strains from the negative test panel amplified with the single primer 77-26-111.

During the search for O157:H7 specific primers it was observed that a significant number of single primers were capable of producing product specific to O157:H7. One such primer was 77-26-111 (Table II), which produced a 962 bp product (SEQ ID NO.: 12). FIGS. 3a and 3b show the banding patterns as separated by gel electrophoresis for samples of 21 different E. coli from both the positive (FIG. 3a) and negative (FIG. 3b) test panels which was amplified with a single primer, 77-26-111. The lanes in FIG. 3a are correlated with the E. coli as follows:

| Lane | Stain No. | Serotype | Lane | Stain No. | Serotype |
|---|---|---|---|---|---|
| 1 | 1450 | O157:H7 | 12 | 1973 | O157:H7 |
| 2 | 1451 | O157:H7 | 13 | 1974 | O157:H7 |
| 3 | 1453 | O157:H7 | 14 | 1975 | O157:H7 |
| 4 | 1454 | O157:H7 | 15 | 1976 | O157:H7 |
| 5 | 1456 | O157:H7 | 16 | 1978 | O157:H7 |
| 6 | 1457 | O157:H7 | 17 | 1980 | O157:H7 |
| 7 | 1458 | O157:H7 | 18 | 1981 | O157:H7 |
| 8 | 1460 | O157:H7 | 19 | 1982 | O157:H7 |
| 9 | 1461 | O157:H7 | 20 | 1983 | O157:H7 |
| 10 | 1462 | O157:H7 | 21 | 1984 | O157:H7 |
| 11 | 1463 | O157:H7 | | | |

The lanes in FIG. 3b are correlated with the E. coli as follows:

| Lane | Stain No. | Serotype | Lane | Stain No. | Serotype |
|---|---|---|---|---|---|
| 1 | 1927 | O111:H IM | 12 | 2433 | O163:H19 |
| 2 | 1972 | O157:H7 | 13 | 2436 | O91:HNM |
| 3 | 1992 | O142:HNM | 14 | 2439 | O145:HNM |
| 4 | 1997 | O20:HNM | 15 | 2441 | O117:H4 |
| 5 | 1999 | O29:HNM | 16 | 2445 | O113:H21 |
| 6 | 2001 | O143:HNM | 17 | 2451 | O135:HNM |
| 7 | 2002 | O115:HNM | 18 | 2455 | O118:H12 |
| 8 | 2034 | O115:HNM | 19 | 2456 | O126:HNM |
| 9 | 2036 | O115:HNM | 20 | 2457 | O146:H21 |
| 10 | 2037 | O115:HNM | 21 | 2458 | O121:HNM |
| 11 | 2431 | O167:H5 | 22 | 2459 | O113:H21 |

Unlabeled lanes contain molecular weight markers of the following sizes: 228, 412, 693, 1331, and 2306 bps.

Amplification conditions using primer 77-26-111 for amplification of genomic DNA from the positive test panel (FIG. 3a) were as follows:

For each 50 µL reaction, 1.5 µL - dNTP mix (5 mM dNTP each), 36.3 µL deionized water, 5 µL - 10X reaction buffer (500 mM KCl, 100 mM tris @ pH 8.3, 15 mM MgCl$_2$, 0.003% gelatin), 5 µL - single primer (10 mM), 0.4 µL Taq polymerase (5 U/µL), and 1.2 µL Taq dilution buffer (10 mM tris @ pH 8.0 and 1.0% Tween 20) were combined. 1.0 µL - genomic bacterial DNA @ 50 ng/µL was added. The reaction was heated to 94° C. for 2 minutes. Thirtyfive cycles of the following temperature cycle were run: 15" @ 94° C., 3' @ 72° C. At the conclusion of the cycling the reaction was incubated at 72° C. for 7 minutes. A 5 µL aliquot of the reaction was combined with 2 µL of Ficol-loading buffer and run on a 4% acrylamide gel (29:1)/1.0x TBE.

Amplification conditions using primer 77-26-111 for amplification of genomic DNA from the negative test panel (FIG. 3b) were as follows:

For each 50 µL reaction, 1.5 µL - dNTP mix (5 mM dNTP each), 36.3 µL deionized water, 5 µL - 10X reaction buffer (500 mM KCl, 100 mM tris @ pH 8.3, 15 mM MgCl$_2$, 0.003% gelatin), 5 µL - single primer (10 mM), 0.4 µL Taq polymerase (5 U/µL), and 1.2 µL Taq dilution buffer (10 mM tris @ pH 8.0 and 1.0% Tween 20) were combined. 1.0 µL - genomic bacterial DNA @ 50 ng/µL was added. The reaction was heated to 94° C. for 2 minutes. Thirtyfive cycles of the following temperature cycle were run: 15" @ 94° C., 3' @ 72° C. At the conclusion of the cycling the reaction was incubated at 72° C. for 7 minutes. A 5 µL aliquot of the reaction was combined with 2 µL of Ficol-loading buffer and run on a 4% acrylamide gel (29:1)/1.0x TBE.

Areas of the 962 bp product produced by amplification using 77-26-111 were screened for other 0157:H7 specific primers. It was suspected that 0157:H7 specificity arose primarily from the 77-26-111 site on the (−) strand. Since this site was suspected of having less than perfect homology to the primer sequence, priming sites closely surrounding this site were evaluated. These evaluations produced two other priming pairs, 77-26-53817111-26-rc1012 and 77-23-114/77-23-rc536, producing amplification products of 527 bp (SEQ ID NO.: 14) and 467 bp (SEQ ID NO.: 13), respectively.

Figure 4A:
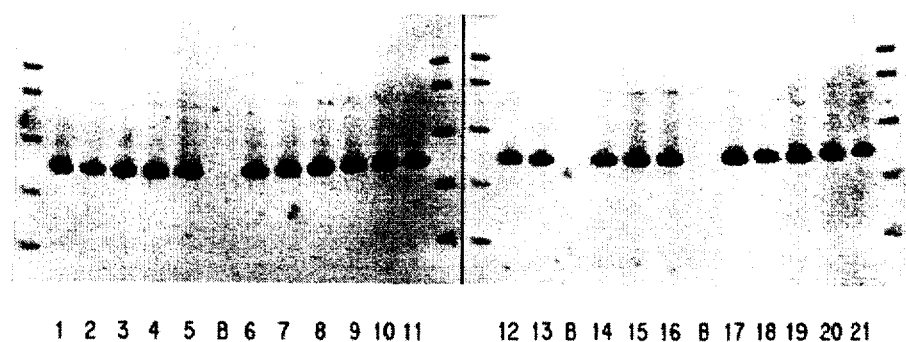
FIG. 4a displays the PCR product patterns of E. coli strains from the positive test panel amplified with the primer pair 77-26-538/7111-26-rc1012.
Figure 4B:
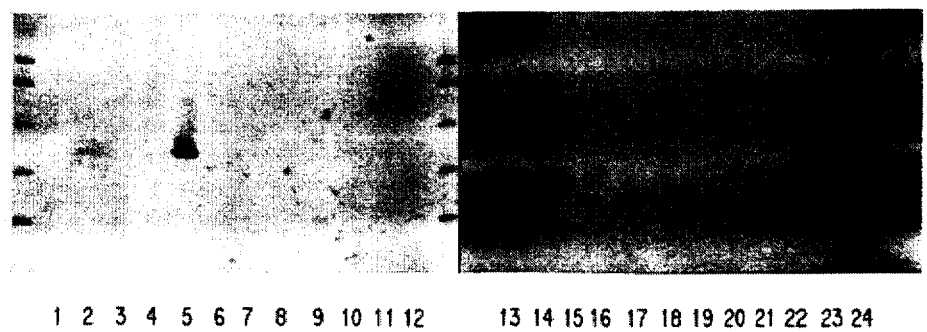
FIG. 4b displays the PCR product patterns of E. coli strains from the negative test panel amplified with the primer pair 77-26-538/7111-26-rc1012.

FIGS. 4a and 4b show the banding patterns as separated by gel electrophoresis for samples of 21 different E. coli from both the positive (FIG. 4a) and negative (FIG. 4b) test panels which resulted from amplification with a single primer, 77-26-111. The lanes in FIG. 4a are correlated with the E. coli as follows:

| Lane | Stain No. | Serotype | Lane | Stain No. | Serotype |
|---|---|---|---|---|---|
| 1 | 1450 | 0157:H7 | 12 | 8295 | 0157:H7 |
| 2 | 1451 | 0157:H7 | 13 | 8296 | 0157:H7 |
| 3 | 1453 | 0157:H7 | 14 | 8298 | 0157:H7 |
| 4 | 1454 | 0157:H7 | 15 | 8299 | 0157:H7 |
| 5 | 1456 | 0157:H7 | 16 | 8300 | 0157:H7 |
| 6 | 1457 | 0157:H7 | 17 | 8857 | 0157:H7 |
| 7 | 1458 | 0157:H7 | 18 | 8858 | 0157:H7 |
| 8 | 1460 | 0157:H7 | 19 | 8859 | 0157:H7 |
| 9 | 1461 | 0157:H7 | 20 | 8860 | 0157:H7 |
| 10 | 1462 | 0157:H7 | 21 | 8861 | 0157:H7 |
| 11 | 1463 | 0157:H7 | | | |

The lanes in FIG. 4b are correlated with the E. coli as follows:

| Lane | Stain No. | Serotype | Lane | Stain No. | Serotype |
|---|---|---|---|---|---|
| 1 | 1732 | 0143:HNM | 12 | 1797 | 0111:HNM |
| 2 | 1733 | 0142:H6 | 13 | 1798 | 028:HNM |
| 3 | 1734 | 0124:H30 | 14 | 1800 | 0128:HNM |
| 4 | 1735 | 0144:HNM | 15 | 1805 | 0143:HNM |
| 5 | 1450 | 0157:H7 | 16 | 1808 | 0111:HNM |
| 6 | 1757 | 0152:HNM | 17 | 1809 | 0111:HNM |
| 7 | 1760 | 06:H1 | 18 | 1813 | 020:HNM |
| 8 | 1762 | 0164:HNM | 19 | 1814 | 06:H- |
| 9 | 1763 | 020:HNM | 20 | 1827 | 020:HNM |
| 10 | 1771 | 0148:H28 | 21 | 1828 | 0143:HNM |
| 11 | 1772 | 0159:H20 | 22 | 1883 | 0125:HNM |
| 11 | 1796 | 086:HNM | 22 | 1886 | 0164:HNM |

Unabeled lanes contain molecular weight markers of the following sizes: 228, 412, 693, 1331, and 2306 bps.

Amplification conditions using primer pair 77-26-538/7111-26-rc1012 for amplification of genomic DNA from the positive test panel (FIG. 4a) were as follows:

For each 50 μL reaction, 1.5 μL - dNTP mix (5 mM dNTP each), 36.3 μL deionized water, 5 μL - 10X reaction buffer (500 mM KCl, 100 mM tris @ pH 8.3, 15 mM MgCl$_2$, 0.003% gelatin), 2.5 μL - of each primer (10 mM), 0.4 μL Taq polymerase (5 U/μL), and 1.2 μL Taq dilution buffer (10 mM tris @ pH 8.0 and 1.0% Tween 20) were combined. 1.0 μL - genomic bacterial DNA @ 50 ng/μL was added. The reaction was heated to 94° C. for 2 minutes. Thirtyfive cycles of the following temperature cycle were run: 15" @ 94° C., 3' @ 72° C. At the conclusion of the cycling the reaction was incubated at 72° C. for 7 minutes. A 5 μL aliquot of the reaction was combined with 2 μL of Ficol-loading buffer and run on a 4% acrylamide gel (29:1)/1.0x TBE.

Amplification conditions using primer pair 77-26-538/7111-26-rc1012 for amplification of genomic DNA from the negative test panel (FIG. 4b) were as follows:

For each 50 μL reaction, 1.5 μL - dNTP mix (5 mM dNTP each), 36.3 μL deionized water, 5 μL - 10X reaction buffer (500 mM KCl, 100 mM tris @ pH 8.3, 15 mM MgCl$_2$, 0.003% gelatin), 2.5 μL - each primer (10 mM), 0.4 μL Taq polymerase (5 U/μL), and 1.2 μL Taq dilution buffer (10 mM tris @ pH 8.0 and 1.0% Tween 20) were combined. 1.0 μL - genomic bacterial DNA @ 50 ng/μL was added. The reaction was heated to 94° C. for 2 minutes. Thirtyfive cycles of the following temperature cycle were run; 15" @ 94° C., 3' @ 72° C. At the conclusion of the cycling the reaction was incubated at 72° C. for 7 minutes. A 5 μL aliquot of the reaction was combined with 2 μL of Ficol-loading buffer and run on a 4% acrylamide gel (29:1)/1.0x TBE.

Figure 5:
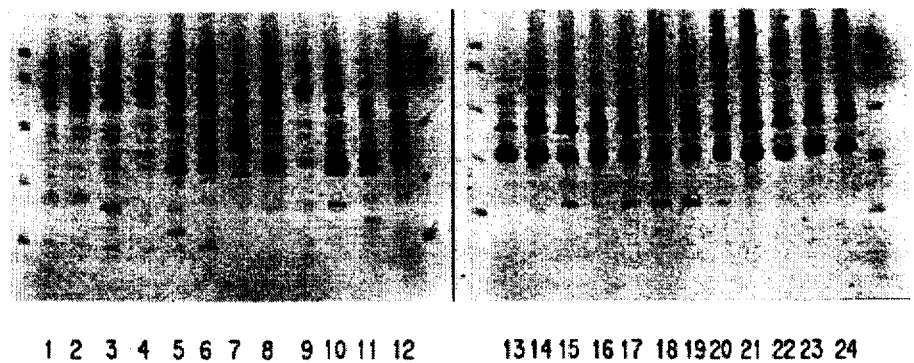
FIG. 5 displays the PCR product patterns of E. coli strains from both the positive and negative test panels amplified with the primer pair 77-23-114/77-23-rc536.

FIG. 5 shows the banding patterns as separated by gel electrophoresis for samples of 24 different E. coli from both the positive and negative test panels which resulted from amplification with the primer pair 77-23-114/77-23-rc536. The lanes in FIG. 5 are correlated with the E. coli as follows:

| Lane | Stain No. | Serotype | Lane | Stain No. | Serotype |
|---|---|---|---|---|---|
| 1 | 1721 | 0114:H32 | 13 | 640 | 0157:H7 |
| 2 | 1770 | 0115:H8 | 14 | 641 | 0157:H7 |
| 3 | 1794 | NOT TYPED | 15 | 642 | 0157:H7 |
| 4 | 1821 | 055:H- | 16 | 914 | 0157:H7 |
| 5 | 1831 | 026:H11 | 17 | 915 | 0157:H7 |
| 6 | 1854 | 044 | 18 | 916 | 0157:H7 |
| 7 | 1860 | 0126:H27 | 19 | 935 | 0157:H7 |
| 8 | 1922 | 063:H6 | 20 | 1449 | 0157:H7 |
| 9 | 2462 | 0153:H25 | 21 | 1455 | 0157:H7 |
| 10 | 2464 | 0126:HNM | 22 | 1459 | 0157:H7 |
| 11 | 3129 | 075 | 23 | 1977 | 0157:H7 |
| 12 | 5011 | 0111 | 24 | 1979 | 0157:H7 |

Unlabeled lanes contain molecular weight markers of the following sizes: 228, 412, 693, 1331, and 2306 bps.

Amplification conditions using primer pair-23-114/77-23-rc536 for amplification of genomic DNA from both the positive and negative test panel were as follows:

For each 50 μL reaction, 1.5 μL - dNTP mix (5 mM dNTP each), 36.3 μL deionized water, 5 μL - 10X reaction buffer (500 mM KCl, 100 mM tris @ 8.3, 15 mM MgCl$_2$, 0.003% gelatin), 2.5 μL - each primer (10 mM), 0.4 μL Taq polymerase (5 U/μL), and 1.2 μL Taq dilution buffer (10 mM tris @ pH 8.0 and 1.0% Tween 20) were combined. 1.0 μL - genomic bacterial DNA @ 50 ng/μL was added. The reaction was heated to 94° C. for 2 minutes. Thirtyfive cycles of the following temperature cycle were run: 15" @ 94° C., 2' @ 65° C., and 1' @ 72° C. At the conclusion of the cycling the reaction was incubated at 72° C. for 7 minutes. A 5 μL aliquot of the reaction was combined with 2 μL of Ficol-loading buffer and run on a 4% acrylamide gel (29:1)/1.0x TBE.

What is claimed is:

1. A method of determining whether an unknown microorganism is a member of the *Escherichia coli* O157:H7 serotype, comprising analyzing the genomic DNA of said unknown microorganism to detect the presence of a nucleic acid sequence selected from the group consisting of SEQ ID NO: 1, SEQ ID NO.: 2, and a diagnostic marker fragment thereof, whereby the presence of said nucleic acid sequence indicates said unknown microorganism is a member of said *Escherichia coil* O157:H7 serotype.

2. The method of claim 1 wherein said analyzing step further comprises the substeps of:

(i) performing a PCR amplification reaction on the genomic DNA of said unknown microorganism using a pair of primers comprising a first primer and a second primer wherein said first primer has a nucleic acid sequence derived from SEQ ID NO.: 1 and said second primer has a nucleic acid sequence derived from SEQ ID NO.: 2; and (ii) detecting the presence of DNA which has been amplified by said primer pair of step (i);

whereby the presence of amplified DNA at step (ii) indicates that said unknown microorganism is a member of the Escherichia coli 0157:H7 serotype.

3. The method of claim 2 wherein at substep (i) said first primer is selected from the group of diagnostic marker fragments derived from SEQ ID NO.: 1 consisting of SEQ ID NOS.: 3, 5, 7, and 9, and said second primer is selected from the group of diagnostic marker fragments derived from SEQ ID NO.: 2 consisting of SEQ ID NOS.: 4, 6, 8, and 10.

4. The method of claim 1 wherein said analyzing step further comprises the substeps of a) contacting the genomic DNA of said unknown microorganism with a nucleic acid probe consisting of a nucleic acid sequence which is complementary to and which hybridizes with a nucleic acid sequence selected from the group consisting of SEQ ID NO.: 1, SEQ ID NO.: 2, and a diagnostic marker fragment thereof, and then b) detecting the presence of said nucleic acid probe, the presence of said nucleic acid probe indicating the presence of said nucleic acid sequence in turn indicating that said unknown microorganism is a member of the *Escherichia coli* 0157:H7 serotype.

5. An isolated nucleic acid fragment having SEQ ID NO.: 1 or a diagnostic marker fragment thereof.

6. An isolated nucleic acid fragment having SEQ ID NO.: 2 or a diagnostic marker fragment thereof.

7. An isolated nucleic acid fragment selected from the group of nucleic acid sequences consisting of SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, and SEQ ID NO.: 14.

* * * * *

UNITED STATES PATENT AND TRADEMARK OFFICE
CERTIFICATE OF CORRECTION

PATENT NO. : 5,747,257
DATED : May 5, 1998
INVENTOR(S) : Mark Anton Jensen

It is certified that error appears in the above-identified patent and that said Letters Patent is hereby corrected as shown below:

Column 11, line 42, change "0157:117" to --0157:H7--.

Column 11, line 29, change "Stain No." to --Strain No.--.

Column 13, line 58, change "Stain No." to --Strain No.--.

Column 14, line 3, change "Stain No." to --Strain No.--.

Column 15, lines 19 and 34, change "Stain No." to --Strain No.--.

Column 16, line 26, change "Stain No." to --Strain No.--.

Column 28, line 65, change "coil" to --coli--.

Signed and Sealed this

Eleventh Day of January, 2000

Attest:

Q. TODD DICKINSON

*Attesting Officer*   *Acting Commissioner of Patents and Trademarks*

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 1047 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GGCATTAGTC ACGCAATGAA TGGCACACAG GAGCGTGAAT TATCGCTGGC TGAATTATCC      60
TGGTGGGCGG CCTGCAATCA GGTGGTGGAT GCACTACCTG AGGCAGTAGC GCGTCGTTCG     120
CTGGGATTAC CAGCGGAAAA AATCCGCTCC GTATACCGTG AGAGTGACAT CGCACCGGGA     180
GAACAGACAG CCATCAGCAT ACTGAAGCAG CGCACAAAAA ATATTGCGCT GCCACTTCAC     240
GTCCACCAGC AACAAAATCC ACCACAGAAA AAACGGTTG TCAGTATCGC CGTTGATCCG      300
GAGTCTCCTG AATCGTTCAT GAGGCGGCCT AAACGTTGCC GCTGGGTTAA TGAGAAATAC     360
ACGCGCTGGG TAAAGACACA GCCGTGTGCG TGTTGTGGTA AGCCTGCTGA CGATCCGCAT     420
CACCTGATTG GTCATGGTCA GGGGGGAATG GGGACAAAGG CCCACGATAT TTTCACGCTA     480
CCGTTGTGCC GGGAGCACCA CAACGAACTT CATGCAGACC CGCTGGAGTT TGAGAAAAAG     540
TACGGCTCTC AGATTGAGTT AATTTTTCGT TTTCTTGATC ACGCCTTTGC GACTGGCGTG     600
CTCGGGTAAA AGAGGTGACT GATGCTCATA GATTTGGTTT TACCTTACCC GCCGACGGTG     660
AACACCTACT GGCGACGTCG TGGCAGCACA TATTTTGTAT CAAAAGCCGG TGAGCGTTAT     720
CGCCGGGCTG TGGCGCTTAT TGTTCGCCAG CAGCGGCTGA AATTAAGCCT GTCCGGAAGG     780
CTGGCGATGA AGATTATTGC CGAGCCACCG GATAAGCGCC GCCGTGACCT GGACAATGTT     840
CTGAAAGCGC CGCTGGATGC GCTGACGCAT GCGGGGTTGC TAATGGACGA TGAGCAGTTT     900
GATGAAATCA ATATTGTGCG CGGTCAGCTC GTTCCTGGTG AGCGGCTGGG GATAAAAATC     960
ACAGAACTGG AGTGCGCATG AATAACCACT ATTTACAGTT TGTGCGTGAG CTGCTCATTA    1020
TCGCTACTGC CTCAGGTAGT GCATCCA                                        1047
```

( 2 ) INFORMATION FOR SEQ ID NO:2:

( i ) SEQUENCE CHARACTERISTICS:
        ( A ) LENGTH: 1047 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
TGGATGCACT ACCTGAGGCA GTAGCGATAA TGAGCAGCTC ACGCACAAAC TGTAAATAGT      60
GGTTATTCAT GCGCACTCCA GTTCTGTGAT TTTTATCCCC AGCCGCTCAC CAGGAACGAG     120
CTGACCGCGC ACAATATTGA TTTCATCAAA CTGCTCATCG TCCATTAGCA ACCCCGCATG     180
CGTCAGCGCA TCCAGCGGCG CTTTCAGAAC ATTGTCCAGG TCACGGCGGC GCTTATCCGG     240
TGGCTCGGCA ATAATCTTCA TCGCCAGCCT TCCGGACAGG CTTAATTTCA GCCGCTGCTG     300
GCGAACAATA AGCGCCACAG CCCGGCGATA ACGCTCACCG GCTTTTGATA CAAAATATGT     360
```

-continued

```
GCTGCCACGA CGTCGCCAGT AGGTGTTCAC CGTCGGCGGG TAAGGTAAAA CCAAATCTAT      420
GAGCATCAGT CACCTCTTTT ACCCGAGCAC GCCAGTCGCA AAGGCGTGAT CAAGAAAACG      480
AAAAATTAAC TCAATCTGAG AGCCGTACTT TTTCTCAAAC TCCAGCGGGT CTGCATGAAG      540
TTCGTTGTGG TGCTCCCGGC ACAACGGTAG CGTGAAAATA CGTGGGCCT TTGTCCCCAT       600
TCCCCCCTGA CCATGACCAA TCAGGTGATG CGGATCGTCA GCAGGCTTAC CACAACACGC      660
ACACGGCTGT GTCTTTACCC AGCGCGTGTA TTTCTCATTA ACCCAGCGGC AACGTTTAGG      720
CCGCCTCATG AACGATTCAG GAGACTCCGG ATCAACGGCG ATACTGACAA CCGTTTTTT      780
CTGTGGTGGA TTTTGTTGCT GGTGGACGTG AAGTGGCAGC GCAATATTTT TTGTGCGCTG      840
CTTCAGTATG CTGATGGCTG TCTGTTCTCC CGGTGCGATG TCACTCTCAC GGTATACGGA      900
GCGGATTTTT TCCGCTGGTA ATCCAGCGA ACGACGCGCT ACTGCCTCAG GTAGTGCATC       960
CACCACCTGA TTGCAGGCCG CCCACCAGGA TAATTCAGCC AGCGATAATT CACGCTCCTG      1020
TGTGCCATTC ATTGCGTGAC TAATGCC                                         1047
```

(2) INFORMATION FOR SEQ ID NO:3:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
GGCATTAGTC AC                                                          12
```

(2) INFORMATION FOR SEQ ID NO:4:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
GTGACTAATG CC                                                          12
```

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
TGGATGCACT ACCTGAGGCA GTAGCG                                           26
```

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

( x i ) SEQUENCE DESCRIPTION: SEQ ID NO:6:

CGCTACTGCC TCAGGTAGTG CATCCA    26

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CACTACCTGA GGCAGTAGCG CGT    23

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CTCAATCTGA GAGCCGTACT TTT    23

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

ATGCAGACCC GCTGGAGTTT GAGAAA    26

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

TACCTGAGGC AGTAGCGATA ATGAGC    26

( 2 ) INFORMATION FOR SEQ ID NO:11:

( i ) SEQUENCE CHARACTERISTICS:
        ( A ) LENGTH: 626 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GGCATTAGTC ACGCAATGAA TGGCACACAG GAGCGTGAAT TATCGCTGGC TGAATTATCC    60

| | | | | | |
|---|---|---|---|---|---|
| TGGTGGGCGG | CCTGCAATCA | GGTGGTGGAT | GCACTACCTG | AGGCAGTAGC | GCGTCGTTCG | 120 |
| CTGGGATTAC | CAGCGGAAAA | AATCCGCTCC | GTATACCGTG | AGAGTGACAT | CGCACCGGGA | 180 |
| GAACAGACAG | CCATCAGCAT | ACTGAAGCAG | CGCACAAAAA | ATATTGCGCT | GCCACTTCAC | 240 |
| GTCCACCAGC | AACAAAATCC | ACCACAGAAA | AAAACGGTTG | TCAGTATCGC | CGTTGATCCG | 300 |
| GAGTCTCCTG | AATCGTTCAT | GAGGCGGCCT | AAACGTTGCC | GCTGGGTTAA | TGAGAAATAC | 360 |
| ACGCGCTGGG | TAAAGACACA | GCCGTGTGCG | TGTTGTGGTA | AGCCTGCTGA | CGATCCGCAT | 420 |
| CACCTGATTG | GTCATGGTCA | GGGGGGAATG | GGGACAAAGG | CCCACGATAT | TTTCACGCTA | 480 |
| CCGTTGTGCC | GGGAGCACCA | CAACGAACTT | CATGCAGACC | CGCTGGAGTT | TGAGAAAAAG | 540 |
| TACGGCTCTC | AGATTGAGTT | AATTTTTCGT | TTTCTTGATC | ACGCCTTTGC | GACTGGCGTG | 600 |
| CTCGGGTAAA | AGAGGTGACT | GATGCT | | | | 626 |

( 2 ) INFORMATION FOR SEQ ID NO:12:

( i ) SEQUENCE CHARACTERISTICS:
        ( A ) LENGTH: 962 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

| | | | | | |
|---|---|---|---|---|---|
| TGGATGCACT | ACCTGAGGCA | GTAGCGCGTC | GTTCGCTGGG | ATTACCAGCG | GAAAAAATCC | 60 |
| GCTCCGTATA | CCGTGAGAGT | GACATCGCAC | CGGGAGAACA | GACAGCCATC | AGCATACTGA | 120 |
| AGCAGCGCAC | AAAAAATATT | GCGCTGCCAC | TTCACGTCCA | CCAGCAACAA | AATCCACCAC | 180 |
| AGAAAAAAAC | GGTTGTCAGT | ATCGCCGTTG | ATCCGGAGTC | TCCTGAATCG | TTCATGAGGC | 240 |
| GGCCTAAACG | TTGCCGCTGG | GTTAATGAGA | AATACACGCG | CTGGGTAAAG | ACACAGCCGT | 300 |
| GTGCGTGTTG | TGGTAAGCCT | GCTGACGATC | CGCATCACCT | GATTGGTCAT | GGTCAGGGGG | 360 |
| GAATGGGGAC | AAAGGCCCAC | GATATTTTCA | CGCTACCGTT | GTGCCGGGAG | CACCACAACG | 420 |
| AACTTCATGC | AGACCCGCTG | GAGTTTGAGA | AAAAGTACGG | CTCTCAGATT | GAGTTAATTT | 480 |
| TTCGTTTTCT | TGATCACGCC | TTTGCGACTG | GCGTGCTCGG | GTAAAAGAGG | TGACTGATGC | 540 |
| TCATAGATTT | GGTTTTACCT | TACCCGCCGA | CGGTGAACAC | CTACTGGCGA | CGTCGTGGCA | 600 |
| GCACATATTT | TGTATCAAAA | GCCGGTGAGC | GTTATCGCCG | GGCTGTGGCG | CTTATTGTTC | 660 |
| GCCAGCAGCG | GCTGAAATTA | AGCCTGTCCG | GAAGGCTGGC | GATGAAGATT | ATTGCCGAGC | 720 |
| CACCGGATAA | GCGCCGCCGT | GACCTGGACA | ATGTTCTGAA | AGCGCCGCTG | GATGCGCTGA | 780 |
| CGCATGCGGG | GTTGCTAATG | GACGATGAGC | AGTTTGATGA | AATCAATATT | GTGCGCGGTC | 840 |
| AGCTCGTTCC | TGGTGAGCGG | CTGGGGATAA | AAATCACAGA | ACTGGAGTGC | GCATGAATAA | 900 |
| CCACTATTTA | CAGTTTGTGC | GTGAGCTGCT | CATTATCGCT | ACTGCCTCAG | GTAGTGCATC | 960 |
| CA | | | | | | 962 |

( 2 ) INFORMATION FOR SEQ ID NO:13:

( i ) SEQUENCE CHARACTERISTICS:
        ( A ) LENGTH: 467 base pairs
        ( B ) TYPE: Nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

| | | | | | | |
|---|---|---|---|---|---|---|
| CACTACCTGA | GGCAGTAGCG | CGTCGTTCGC | TGGGATTACC | AGCGGAAAAA | ATCCGCTCCG | 60 |
| TATACCGTGA | GAGTGACATC | GCACCGGGAG | AACAGACAGC | CATCAGCATA | CTGAAGCAGC | 120 |
| GCACAAAAAA | TATTGCGCTG | CCACTTCACG | TCCACCAGCA | ACAAAATCCA | CCACAGAAAA | 180 |
| AAACGGTTGT | CAGTATCGCC | GTTGATCCGG | AGTCTCCTGA | ATCGTTCATG | AGGCGGCCTA | 240 |
| AACGTTGCCG | CTGGGTTAAT | GAGAAATACA | CGCGCTGGGT | AAAGACACAG | CCGTGTGCGT | 300 |
| GTTGTGGTAA | GCCTGCTGAC | GATCCGCATC | ACCTGATTGG | TCATGGTCAG | GGGGGAATGG | 360 |
| GGACAAAGGC | CCACGATATT | TTCACGCTAC | CGTTGTGCCG | GGAGCACCAC | AACGAACTTC | 420 |
| ATGCAGACCC | GCTGGAGTTT | GAGAAAAAGT | ACGGCTCTCA | GATTGAG | | 467 |

( 2 ) INFORMATION FOR SEQ ID NO:14:

( i ) SEQUENCE CHARACTERISTICS:
        ( A ) LENGTH: 527 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

| | | | | | | |
|---|---|---|---|---|---|---|
| ATGCAGACCC | GCTGGAGTTT | GAGAAAAAGT | ACGGCTCTCA | GATTGAGTTA | ATTTTTCGTT | 60 |
| TTCTTGATCA | CGCCTTTGCG | ACTGGCGTGC | TCGGGTAAAA | GAGGTGACTG | ATGCTCATAG | 120 |
| ATTTGGTTTT | ACCTTACCCG | CCGACGGTGA | ACACCTACTG | GCGACGTCGT | GGCAGCACAT | 180 |
| ATTTGTATC | AAAAGCCGGT | GAGCGTTATC | GCCGGGCTGT | GGCGCTTATT | GTTCGCCAGC | 240 |
| AGCGGCTGAA | ATTAAGCCTG | TCCGGAAGGC | TGGCGATGAA | GATTATTGCC | GAGCCACCGG | 300 |
| ATAAGCGCCG | CCGTGACCTG | GACAATGTTC | TGAAAGCGCC | GCTGGATGCG | CTGACGCATG | 360 |
| CGGGGTTGCT | AATGGACGAT | GAGCAGTTTG | ATGAAATCAA | TATTGTGCGC | GGTCAGCTCG | 420 |
| TTCCTGGTGA | GCGGCTGGGG | ATAAAAATCA | CAGAACTGGA | GTGCGCATGA | ATAACCACTA | 480 |
| TTTACAGTTT | GTGCGTGAGC | TGCTCATTAT | CGCTACTGCC | TCAGGTA | | 527 |

( 2 ) INFORMATION FOR SEQ ID NO:15:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

| | | |
|---|---|---|
| AGCTGATGCT | AC | 12 |

( 2 ) INFORMATION FOR SEQ ID NO:16:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

| | | |
|---|---|---|
| AGTCGAACTG | TC | 12 |

( 2 ) INFORMATION FOR SEQ ID NO:17:

```
        ( i ) SEQUENCE CHARACTERISTICS:
                ( A ) LENGTH: 12 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:17:

TTAGTCACGG CA                                                                                    12

( 2 ) INFORMATION FOR SEQ ID NO:18:

( i ) SEQUENCE CHARACTERISTICS:
                ( A ) LENGTH: 12 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:18:

TGCGATACCG TA                                                                                    12

( 2 ) INFORMATION FOR SEQ ID NO:19:

( i ) SEQUENCE CHARACTERISTICS:
                ( A ) LENGTH: 12 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:19:

CTACAGCTGA TG                                                                                    12

( 2 ) INFORMATION FOR SEQ ID NO:20:

( i ) SEQUENCE CHARACTERISTICS:
                ( A ) LENGTH: 12 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:20:

GTCAGTCGAA CT                                                                                    12

( 2 ) INFORMATION FOR SEQ ID NO:21:

( i ) SEQUENCE CHARACTERISTICS:
                ( A ) LENGTH: 12 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:21:

CGTATGCGAT AC                                                                                    12
```